United States Patent
Gustavsson et al.

(10) Patent No.: US 7,033,609 B2
(45) Date of Patent: *Apr. 25, 2006

(54) MICROPARTICLE PREPARATION

(75) Inventors: Nils Ove Gustavsson, Löddeköpinge (SE); Monica Jönsson, Bara (SE); Timo Laakso, Campton (GB); Mats Reslow, Lund (SE); Sören Björn, Lyngby (DK); Jörn Drustrup, Farum (DK)

(73) Assignee: Jagotec AG, Muttenz (CH)

( * ) Notice: Subject to any disclaimer, the term of this patent is extended or adjusted under 35 U.S.C. 154(b) by 468 days.

This patent is subject to a terminal disclaimer.

(21) Appl. No.: 09/970,792

(22) Filed: Jan. 10, 2002

(65) Prior Publication Data

US 2002/0102311 A1 Aug. 1, 2002

Related U.S. Application Data

(60) Provisional application No. 60/260,495, filed on Jan. 8, 2001.

(30) Foreign Application Priority Data

Oct. 6, 2000 (SE) ............................................. 0003614

(51) Int. Cl.
- A61F 9/50 (2006.01)
- B01J 13/02 (2006.01)
- B32B 15/02 (2006.01)

(52) U.S. Cl. ............... 424/499; 427/213.3; 427/213.36; 428/402; 428/403; 264/4.1; 264/4.3; 264/4.6

(58) Field of Classification Search ............. 427/213.3, 427/213.36; 424/497, 499; 428/402, 403; 264/4.1, 4.3, 4.6

See application file for complete search history.

(56) References Cited

U.S. PATENT DOCUMENTS

| 3,691,090 A | 9/1972 | Kitajima et al. |
| 3,737,337 A | 6/1973 | Schnoring et al. |

(Continued)

FOREIGN PATENT DOCUMENTS

| EP | 0 213 303 A2 | 3/1987 |
| EP | 0 540 582 B1 | 8/1994 |
| EP | 0 688 429 B1 | 2/1998 |
| EP | 0 330 180 B2 | 3/1999 |
| JP | 11302156 | 11/1999 |
| WO | WO 90/13780 A1 | 11/1990 |
| WO | WO 93/21008 A1 | 10/1993 |
| WO | WO 94/12158 A1 | 6/1995 |
| WO | WO 96/10042 A1 | 4/1996 |
| WO | WO 97/14408 A1 | 4/1997 |
| WO | WO 99/00425 A1 | 1/1999 |
| WO | WO 99/20253 A1 | 4/1999 |

OTHER PUBLICATIONS

US 5,849,884, 12/1998, Woiszwillo et al. (withdrawn)

"Formation and Isolation of Spherical Fine Protein Microparticles Through Lyophilization of Protein—Poly(ethylene glycol) Aqueous Mixture", Takahiro Morita et al., Pharmaceutical Research, vol. 17, 11, 2000, pp. 1367 to 1373.

(Continued)

*Primary Examiner*—Carlos A. Azpuru
(74) *Attorney, Agent, or Firm*—Mintz, Levin, Cohn, Ferris, Glovsky and Popeo, P.C.

(57) ABSTRACT

A parenterally administrable, biodegradable microparticle preparation containing a biologically active substance which, during the first 24 hours after injection, exhibits a release of the active substance that is less than 25% of the total release, determined from a concentration-time curve in the form of the ratio between the area under the curve during the said first 24 hours and the total area under the curve in question

12 Claims, 2 Drawing Sheets

U.S. PATENT DOCUMENTS

| | | | |
|---|---|---|---|
| 3,881,991 | A | 5/1975 | Kurimotor et al. |
| 4,389,330 | A | 6/1983 | Tice et al. |
| 4,713,249 | A | 12/1987 | Schröder |
| 5,407,609 | A | 4/1995 | Tice et al. |
| 5,455,342 | A | 10/1995 | Redding, Jr. |
| 5,470,582 | A | 11/1995 | Supersaxo et al. |
| 5,578,709 | A | 11/1996 | Woiszwillo et al. |
| 5,622,657 | A | 4/1997 | Takeda et al. |
| 5,654,010 | A | 8/1997 | Johnson et al. |
| 5,667,808 | A | 9/1997 | Johnson et al. |
| 5,753,234 | A | 5/1998 | Lee et al. |
| 5,776,885 | A | 7/1998 | Orsolini et al. |
| 5,942,253 | A | 8/1999 | Gombotz et al. |
| 5,981,719 | A | 11/1999 | Woiszwillo et al. |
| 6,616,948 | B1 * | 9/2003 | Gustavsson et al. ........ 424/497 |

OTHER PUBLICATIONS

Protein encapsulation into biodegradable microspheres by a novel S/O/W encapsulation method using poly(ethylene glycol) as a protein micronization adjuvant, Takahiro Morita et al., Journal of Controlled Release, 69 (2000) pp. 435–444.

Artursson et al., "Characterization of Polyacryl Starch Microparticles as Carriers for Proteins and Drugs," *Journal of Pharmaceutical Sciences*, vol. 73, No. 11, pp. 1507–1513, (1984).

Franssen et al., "A Novel Preparation Method for Polymeric Microparticles Without the Use of Organic Solvents," *International Journal of Pharmaceutics*, vol. 168, pp. 1–7 (1998).

Fu et al., "Visual Evidence of Acidic Environment Within Degrading Poly(lactic–co–glycolic acid) (PLGA) Microspheres" *Pharmaceutical Research*, vol. 17, No. 1, pp. 100–106 (2000).

Laakso et al., "Biodegradable Microspheres IV: Factors Affecting the Distribution and Degradation of Polyacryl Starch Microparticles," *Journal of Pharmaceutical Sciences*, vol. 75, No. 10, pp. 962–967 (1986).

Laakso et al., "Biodegradable Microspheres X: Some Properties of Polyacryl Starch Microparticles Prepared from Acrylic Acid–Esterified Starch," *Journal of Pharmaceutical Sciences*, vol. 76, No. 12, pp. 935–939 (1987).

Schröder, "Crystallized Carbohydrate Spheres as a Slow Release Matrix for Biologically Active Substances," *Biomaterials*, vol. 5, pp. 100–104 (1984).

Schröder, "Crystallized Carbohydrate Spheres for Slow Release and Targeting," *Enzymology*, vol. 112, No. 9, pp. 116–128 (1985).

Stenekes et al., "The Preparation of Dextran Microspheres in an All–Aqueous System: Effect of the Formulation Parameters on Particle Characteristics," *Pharmaceutical Research*, vol. 15, No. 4 pp. 557–561 (1998).

Stjärnkvist et al., "Biodegradable Microspheres XIII: Properties of the Crosslinking Chains in Polyacryl Starch Microparticles," *Journal of Pharmaceutical Sciences*, vol. 78, No. 1, pp. 52–56 (1989).

Agersø et al., "Plasma Concentration of hGH and anti–hGH Antibodies After Subcutaneous Administration of hGH for 3 Weeks to Immunosuppressed Pigs," *J. Pharmacol Toxicol* No. 41 pp. 1–8 (1999).

Johnson et al., "A Month–Long effect From a Single Injection of Microencapsulated Human Growth Hormone," *Nature Medicine*, vol. 2, No. 7 pp. 795–799 (1996).

Putney, "Encapsulation of Proteins for Improved Delivery," Current Opinion in *Chemical Biology*, Nol. 2, pp. 548–552 (1998).

"Clean Package Insert," Nutropin Depot (somatropin(rDNA origin) for injectable suspension], Genentech, Inc., 1 DNA Way, South San Francisco, CA 940–4990, pp. 1–6 (Dec. 13, 1999).

* cited by examiner

MICROPARTICLE PREPARATION

This application claims the benefit of Provisional application No. 60/260,495 filed Jan. 8, 2001.

TECHNICAL FIELD

The present invention lies within the field of galenic formulations for the administration of biologically active substances, more precisely microparticle preparation for regulated release intended for parenteral administration of biologically active substances, especially drugs.

BACKGROUND TO THE INVENTION

Many drugs have to be administered by injection, since they are either subjected to degradation or are insufficiently absorbed when they are given, for example, orally or nasally or by the rectal route. A drug preparation intended for parenteral use has to meet a number of requirements in order to be approved by the regulatory authorities for use on humans. It must therefore be biocompatible and biodegradable and all used substances and their degradation products must be non-toxic. In addition, particulate drugs intended for injection have to be Small enough to pass through the injection needle, which preferably means that they should be smaller than 200 μm. The drug should not be degraded in the preparation to any great extent during production or storage thereof or after administration and should be released in a biologically active form with reproducible kinetics.

One class of polymers which meets the requirements of biocompatibility and biodegradation into harmless end products is the linear polyesters based on lactic acid, glycolic acid and mixtures thereof. These polymers will also hereinafter be referred to as PLGA. PLGA is degraded by ester hydrolysis in-to lactic acid and glycolic acid and has been shown to possess excellent biocompatibility. The innocuous nature of PLGA can be exemplified, moreover, by the approval by the regulating authorities, including the US Food and Drug Administration, of several parenteral delayed release preparations based on these polymers.

Parenterally administrable delayed release products currently on the market and based on PLGA include Decapeptyl™ (Ibsen Biotech), Prostap SR™ (Lederle), Decapeptyl® Depot (Ferring) and Zoladex® (Zeneca). The drugs in these preparations are all peptides. In other words, they consist of amino acids condensed into a polymer having a relatively low degree of polymerization and they do not have any well-defined three-dimensional structure. This, in turn, usually allows the use of relatively stringent conditions during the production of these products. For example, extrusion and subsequent size-reduction can be utilized, which techniques would probably not be allowed in connection with proteins, since these do not, generally speaking, withstand such stringent conditions.

Consequently, there is also a need for controlled release preparations for proteins. Proteins are similar to peptides in that they also consist of amino acids, but the molecules are larger and the majority of proteins are dependent on a well-defined three-dimensional structure as regards many of their properties, including biological activity and immunogenicity. Their three-dimensional structure can be destroyed relatively easily, for example by high temperatures, surface-induced denaturation and, in many cases, exposure to organic solvents. A very serious drawback connected with the use of PLGA, which is an excellent material per se, for delayed release of proteins is therefore the need to use organic solvents to dissolve the said PLGA, with the attendant risk that the stability of the protein will be compromised and that conformation changes in the protein will lead to an immunological reaction in the patient, which can produce both a loss of therapeutic effect, through the formation of inhibitory antibodies, and toxic side effects. Since it is extremely difficult to determine with certainty whether a complex protein has retained its three-dimensional structure in every respect, it is very important to avoid exposing the protein to conditions which might induce conformation changes.

Despite intense efforts aimed at modifying the PLGA technology in order to avoid this inherent problem of protein instability during the production process, progress within this field has been very slow, the main reason probably being that the three-dimensional structures for the majority of proteins are far too sensitive to withstand the manufacturing conditions used and the chemically acidic environment formed with the degradation of PLGA matricea. The scientific literature contains a large number of descriptions of stability problems in the manufacture of microspheres of PLGA owing to exposure to organic solvents. As an example of the acidic environment which is formed upon the degradation of PLGA matrices, it has recently been shown that the pH value in a PLGA microsphere having a diameter of about 40 μm falls to 1.5, which is fully sufficient to denature, or otherwise damage, many therapeutically usable proteins (Fu et al, Visual Evidence of Acidic Environment Within Degrading Poly(lactic-co-glycolic acid) (PLGA) Microspheres, Pharmaceutical Research, vol. 17, No. 1, 2000, 100–106). Should the microspheres have a greater diameter, the pH value can be expected to fall further owing to the fact that the acidic degradation products then get more difficult to diffuse away and the autocatalytic reaction is intensified.

The technique which is currently most commonly used to encapsulate water-soluble substances, such as proteins and peptides, is the use of multiple emulsion systems. The drug substance is dissolved in an aqueous or buffer solution and subsequently mixed with an organic solvent, immiscible with water, containing the dissolved polymer. An emulsion is formed which has the aqueous phase as the inner phase. Different types of emulsifiers and vigorous mixing are often used to create this first emulsion. This emulsion is then transferred, under agitation, to another liquid, usually water, containing another polymer, for example polyvinyl alcohol, which produces a water/oil/water triple emulsion. The microspheres are next hardened in some way. The most common way is to utilize an organic solvent having a low boiling point, typically dichloromethane, and to distil off the solvent. If the organic solvent is not fully immiscible with water, a continuous extraction procedure can be used by adding more water to the triple emulsion. A number of variations of this general procedure are also described in the literature. In certain cases, the primary emulsion is mixed with a non-aqueous phase, for example silicone oil. Solid drug materials can also be used instead of dissolved ones.

PLGA microspheres containing proteins are described in WO-A1-9013780, in which the main feature is the use of very low temperatures during the production of the microspheres for the purpose of preserving high biological activity in the proteins. The activity for encapsulated superoxide dismutation is measured, but only on the part which has been released from the particles. This method has been used to produce PLGA microspheres containing human growth hormone in WO-A1-9412158, wherein human growth hormone is dispersed in methylene chloride containing PLGA, the obtained dispersion is sprayed into a container of frozen ethanol beneath a layer of liquid nitrogen in order to freeze the fine droplets and said droplets are allowed to settle in the nitrogen on the ethanol, The ethanol is subsequently thawed and the microspheres start to sink in the ethanol, where the methylene chloride is extracted in the ethanol and the microspheres are hardened. Using this methodology, the protein stability can be better retained than in the majority of other processes for enclosing proteins in PLGA microspheres, and a product has also recently been approved by the regulatory authorities in the USA. However, this still remains to be clearly demonstrated for other proteins and the problem remains of exposing the enclosed biologically active substance to a very low pH during the degradation of the PLGA matrix.

In the aforementioned methods based on encapsulation with PLGA, the active substances are still exposed to an organic solvent and this, generally speaking, is harmful to the stability of a protein. Moreover, the discussed emulsion processes are complicated and probably problematical in any attempt to scale up to an industrial scale. Furthermore, many of the organic solvents which are utilized in many of these processes are associated with environmental problems and their high affinity for the PLGA polymer makes their removal difficult.

A number of attempts to solve the above-described problems caused by exposure of the biologically active substance to a chemically acidic environment during the biodegradation of the microsphere matrix and organic solvents in the manufacturing process have been described. In order to avoid an acidic environment during the degradation, attempts have been made to replace PLGA as the matrix for the microspheres by a polymer which produces chemically neutral degradation products, and in order to avoid exposing the biologically active substance to organic solvents, either it has been attempted to manufacture the microrpheres in advance and, only once they have been processed and dried, to load them with the biologically active substance, or attempts have been made to exclude or limit the organic solvent during manufacture of the microspheres.

By way of example, highly branched starch of relatively low molecular weight (maltodextrin, average molecular weight about 5 000 Da) has been covalently modified with acryl groups for conversion of this starch into a form which can be solidified into microspheres and the obtained polyacryl starch has been converted into particulate form by radical polymerization in an emulsion with toluene/chloroform (4:1) as the outer phase (Characterization of Polyacryl Starch Microparticles as Carriers for Proteins and Drugs, Artursson et al, J Pharm Sci, 73, 1507–1513, 1984). Proteins were able to be entrapped in these microspheres, but the manufacturing conditions expose the biologically active substance to both organic solvents and high shearing forces in the Lid manufacture of the emulsion. The obtained microspheres are dissolved enzymatically and the pH can be expected to be kept neutral. The obtained microspheres are not suitable for parenteral administration, especially repeated administrations, for a number of reasons. Most important of all is the incomplete and very slow biodegradability of both the starch matrix (Biodegradable Microspheres IV. Factors Affecting the Distribution and Degradation of Polyacryl Starch Microparticles, Laakso et al, J Pharm Sci 75, 962–967, 1986) and the synthetic polymer chain which cross-links the starch molecules. Moreover, these microspheres are far too small, <2 μm in diameter, to be suitable for injection in the tissues for sustained release, since tissue macrophages can easily phagocytize them. Attempts to raise the degradation rate and the degree of degradation by introducing a potentially biodegradable ester group in order to bond the acryl groups to the highly branched starch failed to produce the intended result and even these polyacryl starch microspheres were biodegraded far too slowly and incompletely over reasonable periods of time (BIODEGRADABLE MICROSPHERES: Some Properties of Polyacryl Starch Microparticles Prepared from Acrylic acid Esterified Starch, Laakso and Sjöholm, 1987 (76), pp. 935–939, J Pharm Sci.)

Microspheres of polyacryl dextran have been manufactured in two-phase aqueous systems (Stenekes et al, The Preparation of Dextran Microspheres in an All-Aqueous System. Effect of the Formulation Parameters on Particle Characteristics, Pharmaceutical Research, Vol. 15, No. 4, 1998, 557–561, and Franssen and Hennink, A novel preparation method for polymeric microparticles without using organic solvents, Int J Pharm 168, 1–7, 1998). With this mode of procedure, the biologically active substance is prevented from being exposed to organic solvents but, for the rest, the microspheres acquire properties equivalent to the properties described for the polyacryl starch microspheres above, which makes them unsuitable for repeated parenteral administrations. Bearing in mind that man does not have specific dextran-degrading enzymes, the degradation rate should be even lower than for polyacryl starch microspheres. The use of dextran is also associated with a certain risk of serious allergic reactions.

Manufacture of starch microspheres with the use of non-chemically-modified starch using an oil as the outer phase has been described (U.S. Pat. No. 4,713,249; Schröder, U., Crystallized carbohydrate spheres for slow release and targeting, Methods Enzymol, 1985 (112), 116–128; Schröder, U., Crystallized carbohydrate spheres as a slow release matrix for biologically active substances, Bio-materials 5:100–104, 1984). The microspheres are solidified in these cases by precipitation in acetone, which leads both to the exposure of the biologically active substance to an organic solvent and to the non-utilization, during the manufacturing process, of the natural tendency of the starch to solidify through physical cross-linking. This leads, in turn, to microspheres having inherent instability, since the starch, after resuspension in water and upon exposure to body fluids, will endeavour to form such cross-links. In order for a water-in-oil emulsion to be obtained, high shear forces are required and the microspheres which are formed are far too small to be suitable for parenteral sustained release.

EP 213303 A2 describes the production of microaspheres of, inter alia, chemically unmodified starch in two-phase aqueous systems, utilizing the natural capacity of the starch to solidify through the formation of physical cross-links, and the immobilization of a substance in these microspheres for the purpose of avoiding exposure of the biologically active substance to organic solvents. The described methodology, in combination with the starch quality which is defined, does not give rise to fully biodegradable particles. Neither are the obtained particles suitable for injection, particularly for repeated injections over a longer period, since the described starch quality contains far too high quantities of foreign vegetable protein. In contrast to what is taught by this patent, it has now also surprisingly been found that significantly better yield and higher loading of the biologically active molecule can be obtained if significantly higher concentrations of the polymers are used than is required to form the two-phase aqueous system and that this also leads to advantages in terms of the conditions for obtaining stable, non-aggregated microspheres and their size distribution. The temperature treatments which are described cannot be used for sensitive macromolecules and the same applies to the processing which comprises drying with either ethanol or acetone Alternative methods for the manufacture of microspheres in two-phase aqueous systems have been described. In U.S. Pat. No. 5,981,719, microparticles are made by mixing the biologically active macromolecule with a polymer at a pH close to the isoelectric point of the macromolecule and stabilizing the microspheres through the supply of energy, preferably heat. The lowest share of macromolecule, i.e. the biologically active substance, in the preparation is 40%, which for most applications is too high and leads to great uncertainty in the injected quantity of active substance, since the dose of microparticles becomes far too low. Even though the manufacturing method is described as mild and capable of retaining the biological activity of the entrapped biologically active substance, the microparticles are stabilized by heating and, in the examples given, heating is effected to at least 58° C. for 30 min. and, in many cases, to 70–90° C. for an equivalent period, which cannot be expected to be tolerated by sensitive proteins, the biological activity of which is dependent on a three-dimensional structure, and even where the protein has apparently withstood the manufacturing process, there is still a risk of small, but nonetheless not insignificant changes in the conformation of the protein. As the outer phase, a combination of two polymers is always used, generally polyvinyl pyrrolidone and PEG, which complicates the manufacturing process in that both these substances must be washed away from the microspheres in a reproducible and reliable manner. The formed microparticles are too small (in the examples, values below 0.1 µm in diameter are quoted) to be suitable for parenteral sustained release after, for example, subcutaneous injection, since macrophages, which are cells which specialize in phagocytizing particles and which are present in the tissues, are easily capable of phagocytizing microspheres up to 5–10, possibly 20 µm, and the phagocytized particles are localized intracellularly in the lysosomes, where both the particles and the biologically active substance are degraded, whereupon the therapeutic effect is lost. The very small particle size also makes the processing of the microspheres more complicated, since desirable methods, such as filtration, cannot be used. The equivalent applies to U.S. Pat. No. 5,849,884.

U.S. Pat. No. 5,578,709 and EP 0 688 429 B1 describe the use of two-phase aqueous systems for the manufacture of macromolecular microparticle solutions and chemical or thermal cross-linking of the dehydrated macromolecules to form microparticles. It is entirely undesirable to chemically cross-link the biologically active macromolecule, either with itself or with the microparticle matrix, since chemical modifications of this kind have a number of serious drawbacks, such as reduction of the bioactivity of a sensitive protein and risk of induction of an immune response to the new antigenic determinants of the protein, giving rise to the need for extensive toxicological studies to investigate the safety of the product. Microparticles which are made through chemical cross-linking with glutaraldehyde are previously known and are considered generally unsuitable for repeated administrations parenterally to humans, The microparticles which are described in U.S. Pat. No. 5,578,709 suffer in general terms from the same drawbacks as are described for U.S. Pat. No. 5,981,719, with unsuitable manufacturing conditions for sensitive proteins, either through their exposure to chemical modification or to harmful temperatures, and a microparticle size distribution which is too narrow for parenteral, sustained release and which complicates post-manufacture processing of the microspheres.

WO 97/14408 describes the use of air-suspension technology for producing microparticles for sustained release after parenteral administration, without the biologically active substance being exposed to organic solvents. However, the publication provides no guidance towards the process according to the invention or towards the novel microparticles which can thereby be obtained.

In U.S. Pat. No. 5,470,582, a microsphere consisting of PLGA and containing a macromolecule is produced by a two-stage process, in which the microsphere as such is first manufactured using organic solvents and then loaded with the macromolecule at a later stage in which the organic solvent has already been removed. This procedure leads to far too low a content of the biologically active substance, generally 1–2%, and to a very large fraction being released immediately after injection, which very often is entirely unsuitable. This far too rapid initial release is already very high given a 1% load and becomes even more pronounced when the active substance content in the microspheres is higher. Upon the degradation of the PLGA matrix, the pH falls to levels which are generally not acceptable for sensitive macromolecules.

A method of controlling the release pattern of (poly) peptides is disclosed in U.S. Pat. No. 5,776,885, said release being accomplished by forming insoluble addition salts thereof. In other words the technique disclosed therein is based on the fact that a water insoluble peptide is released to a lesser extent than its water soluble derivates, which is quite contrary to the technique used in the present invention to properly control the release of generally water soluble substances.

More relevant to illustrate the front line of the art represented by the present invention is Nature Medicine, vol 2, No 7, July 1996, pp 795–799. This document shows that the best result as to release in vivo of microencapsulated human growth hormone before the present invention was made was approximately 30% by weight thereof essentially released within the first 12 hours. Such a release profile has been found to involve a number of side effects and a low therapeutical effect.

That starch is, in theory, a very suitable, perhaps even ideal, matrix material for microparticles has been known for a long time, since starch does not need to be dissolved in organic solvents and has a natural tendency to solidify and since there are enzymes within the body which can break down the starch into endogenic and neutral substances, ultimately glucose, and since starch, presumably owing to the similarity with endogenic glycogen, has been shown to be non-immunogenic. Despite intense efforts, starch having properties which enable manufacture of microparticles suitable for parenteral use and conditions which enable manufacture of fully biodegradable microparticles under mild conditions, which allow sensitive, biologically active substances, such as proteins, to become entrapped, has not been previously described.

Starch granules naturally contain impurities, such as starch proteins, which makes them unsuitable for injection parenterally. In the event of unintentional depositing of insufficiently purified starch, such as can occur in operations where many types of operating gloves are powdered with stabilized starch granules, very serious secondary effects can arise. Neither are starch granules intrinsically suitable for repeated parenteral administrations, for the reason that they are not fully biodegradable within acceptable time spans.

Starch microspheres made of acid-hydrolyzed and purified starch have been used for parenteral administration to humans, The microspheres were made by chemical cross-linking with epichlorohydrin under strongly alkaline conditions. The chemical modification which was then acquired by the starch leads to reduced biodegradability, so that the microspheres can be fully dissolved by endogenic enzymes, such as α-amylase, but not converted fully into glucose as the end product. Neither the manufacturing method nor the obtained microspheres are suitable for the immobilization of sensitive proteins, nor is such acid-hydrolyzed starch, which is essentially based on hydrolyzed amylose, suitable for producing either fully biodegradable starch microspheres or starch microspheres containing a high load of a biologically active substance, such as a protein.

Hydroxyethyl starch (HES) is administered parenterally to humans in high doses as a plasma substitute. HES is produced by starch granules from starch consisting broadly exclusively of highly branched amylopectin, so-called "waxy maize", being acid-hydrolyzed in order to reduce the molecular weight distribution and being subsequently hydroxyethylated under alkaline conditions and acid-hydrolyzed once more to achieve an average molecular weight of around 200,000 Da. After this, filtration, extraction with acetone and spray-drying are carried out. The purpose of the hydroxyethylation is to prolong the duration of the effect, since non-modified amylopectin is very rapidly degraded by α-amylase and its residence time in the circulation is around 10 minutes. HES is not suitable for the production of fully biodegradable microspheres containing a biologically active substance, since the chemical modification leads to a considerable fall in the speed and completeness of the biodegradation and results in the elimination of the natural tendency of the starch to solidify through the formation of non-covalent cross-linkings. Moreover, highly concentrated solutions of HES become far too viscous to be usable for the production of microparticles. The use of HES in these high doses shows that parenterally usable starch can be manufactured, even though HES is not usable for the manufacture of microspheres without chemical cross-linking or precipitation with organic solvents.

WO 99/00425 describes the use of heat-resistant proteolytic enzymes with wide pH-optimum to purge starch granules of surface-associated proteins. The obtained granules are not suitable for parenteral administration, since they still contain the starch proteins which are present within the granules and there is a risk that residues of the added proteolytic enzymes will be left in the granules. Neither are the granules suitable for the manufacture of parenterally administrable starch microspheres in two-phase aqueous systems, since they have the wrong molecular weight distribution to be able to be used in high enough concentration, even after being dissolved, and, where microspheres can be obtained, they are probably not fully biodegradable.

The use of shearing to modify the molecular weight distribution of starch, for the purpose of producing better starch for the production of tablets, is described in U.S. Pat. No. 5,455,342 and WO 93/21008. The starch which is obtained is not suitable for parenteral administration owing to the high content of starch proteins, which might be present in denatured form after the shearing, and neither is the obtained starch suitable for producing biodegradable starch microspheres for parenteral administration or for use in two-phase aqueous systems for the production of such starch microspheres. Shearing has also been used to manufacture hydroxyethylstarch, as is disclosed in WO 96/10042. However, for similar reasons such hydroxyethylstarch is not either suitable for parenteral administration or for the production of microspheres as referred to above.

A process for the production of parenterally administrable microparticles and microparticles having the following features would therefore be extremely desirable:

a process which makes it possible to entrap biologically active substances which are sensitive to or instable in organic solvents, i.e. primarily water-soluble substances, in microparticles with retention of their biological activity;

a process by means of which biologically active substances can be entrapped under conditions which do not expose them to organic solvents, high temperatures or high shear forces and which allows them to retain their biological activity;

a process which permits high loading of a parenterally administrable preparation with even sensitive, biologically active substances;

a process by means of which a substantially fully biodegradable and biocompatible preparation can be produced, which is suitable for injecting parenterally and upon whose degradation chemically neutral endogenic substances are formed;

a process by means of which a parenterally injectable preparation having a size exceeding 20 μm and preferably exceeding 30 μm, is produced for the purpose of avoiding phagocytosis of tissue macrophages and which simplifies processing of the same during manufacture;

a process for the production of microparticles containing a biologically active substance, which microparticles can be used as intermediate product in the production of a preparation for controlled, sustained or delayed release and which permit rigorous quality control of the chemical stability and biological activity of the entrapped biological substance;

a process which utilizes a parenterally acceptable starch which is suitable for the production of substantially fully biodegradable starch microparticles;

a substantially fully biodegradable and biocompatible microparticulate preparation which is suitable for injecting parenterally and upon whose degradation chemically neutral endogenous substances are formed;

a microparticulate preparation containing a biologically active substance and having a particle size distribution which is suitable for coating by means of air suspension technology and having sufficient mechanical strength for this purpose;

a coated microparticulate preparation containing a biologically active substance, which preparation gives a controlled release after parenteral administration, Objects such as these and other objects are achieved by means or the invention defined below.

DESCRIPTION OF THE INVENTION

The present invention relates to a novel microparticle preparation. More specifically it relates to a microparticle preparation which is biodegradable, which contains a biologically active substance that is sensitive to or unstable in organic solvents and which is intended for parenteral administration of the said substance to a mammal, especially a human. The said parenteral administration primarily means that the microparticles are intended for injection.

Since the microparticles are primarily intended for injection, it is a question especially of manufacturing particles with an average diameter within the range of 10–200 μm, generally 20–100 μm and in particular 20–80 μm. The expression "microparticles" is used in connection with the invention as a general designation for particles of a certain size known in the art. One type of microparticles is that of microspheres which have in the main a spherical shape, although the term microparticle may generally include deviations from such an ideal spherical shape. The term microcapsule known in the art is also covered by the expression microparticle in accordance with the known art.

Figure 1:
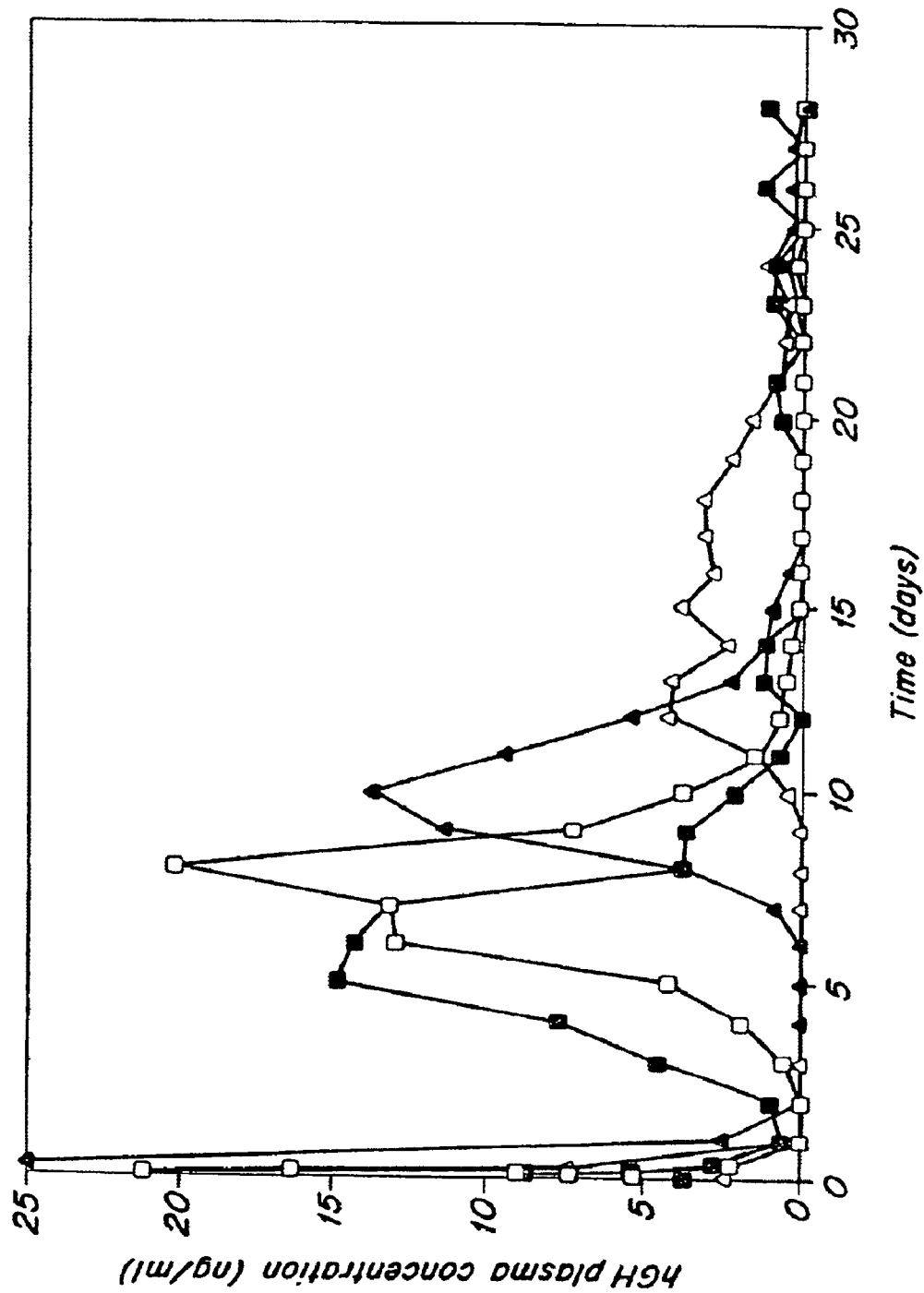
FIGS. 1, 2A, and 2B depict graphs of the relationship of Time in days against the hGH plasma concentration in ng/ml.

According to one aspect of the present invention this provides a parenterally administrable, biodegradable microparticle preparation containing a biologically active substance that is sensitive to or unstable in organic solvents which preparation, during the first 24 hours after injection, exhibits a release of the active substance that is less than 25% of the total release, determined from a concentration-time curve in the form of the ratio between the area under the curve during the first 24 hours and the total area under the curve in question.

The release during the first 24 hours after injection should preferably be less than 20%, more preferably less than 15%, even more preferably less than 10% and most preferably less than 5% of the total release.

According to another aspect of the present invention this provides a microparticle preparation of the aforementioned type which, during the first 48 hours after injection, exhibits a release of the active substance in which the maximum plasma or serum concentration is less than 300% of the maximum concentration of the biologically active substance at any time in excess of 48 hours after injection.

The said maximum concentration is preferably less than 200% and more preferably less than 100% of the maximum concentration in question.

According to still another aspect of the invention last-mentioned preparation exhibits a release as defined for the preparation according to the first aspect of the invention.

Yet a further aspect of the invention is represented by a microparticle preparation of the aforementioned type, in which the microparticles are substantially composed of starch, which has an amylopectin content in excess of 85% by weight, of which at least 80 by weight has an average molecular weight in the range of 10–10 000 kDa, which has an amino acid nitrogen content of less than 50 µg per gram dry weight of starch and which lacks covalent chemical cross-linking between the starch molecules and which exhibits a release of the biologically active substance in which the bioavailability of the said substance is at least 35% of the bioavailability that is obtained when the substance in question is injected intravenously in soluble form, The said bioavailability is preferably at least 45%, more preferably at least 50% of the bioavailability that is obtained when the biologically active substance is injected intravenously.

Another aspect of the present invention is represented by a microparticle preparation of the said type, in which the microparticles are substantially composed of starch, which has an amylopectin content in excess of 85% by weight, of which at least 80% by weight has an average molecular weight in the range of 10–10 000 kDa, which has an amino acid nitrogen content of less than 50 µg per gram dry weight of starch and which lacks covalent chemical cross-linking between the starch molecules and which exhibits a release of the active substance characterized in that in the release that takes place during any continuous seven-day period the quotient for the highest serum or plasma concentration of the biologically active substance divided by the mean concentration during the said seven-day period is less than 5, provided that the chosen seven-day period does not include the first 24 hours after injection.

The said release is preferably less than 4 times, more preferably less than 3 times, and most preferably less than twice.

According to yet another aspect the invention provides a microparticle preparation of the type indicated, in which the microparticles are substantially composed of starch, which has an amylopectin content in excess of 85% by weight, of which at least 80% by weight has an average molecular weight in the range of 10–10 000 kDa, which have an amino acid nitrogen content of less than 50 µg per gram dry weight of starch and which lack covalent chemical cross-linking between the starch molecules and which exhibits a release of the biologically active substance in which the mean residence time for the substance in question is at least 4 days.

The said mean residence time is preferably at least 7 days, more preferably at least 9 days, for example at least 11 days or in particular at least 13 days.

The characteristic features that have been specified for the aspects of the invention described above may be combined in any suitable combinations.

More specifically, the primary factors for the various characteristics specified for the microparticle preparation according to the invention are the terms MRT, burst and bioavailability.

These can be defined as follows:

MRT

An object of preparations for controlled release is to obtain a sustained release of the active material. One measure which can be used to quantify the release time is mean residence time (MRT), which is the recognized term within pharmacokinetics.

MRT is the average time for which the molecules introduced into the body reside within the body. (Clinical Pharmacokinetics. Concepts and Applications. Malcolm Rowland and Thomas M. Tozer, $2^{nd}$ ed., Lea&Febiger, Philadelphia London).

The MRT value can be calculated from plasma concentration data, using the following formula.

$$MRT = \frac{\int_0^\infty tC\,dt}{\int_0^\infty C\,dt}$$

where C is the plasma concentration and t is the time.

Burst

A common problem with controlled release preparations for parenteral use is that a large part of the drug is released during the early phase immediately following administration in the body. Within the specialist literature, this is termed the "burst effect". This is generally due to the fact that the drug is located on the surface of the formulation or that the formulation (which can consist of microparticles) bursts. A low burst effect is very desirable, since a high concentration of drug can be toxic and the part which disappears rapidly in the initial period, moreover, is poorly utilized, which means that more drug is required to maintain a therapeutic level of the drug during the intended treatment period.

Burst is defined as that fraction of the drug which is absorbed during the first 24 hours of the total fraction which is absorbed.

In mathematical terms, it can be defined using "area under curve" calculations from plasma concentration graphs.

$$Burst = \frac{\int_0^{24h} C\,dt}{\int_0^{\infty} C\,dt} \cdot 100\%$$

Bioavailability

Bioavailability is a measure of how large a part of the supplied drug is absorbed in active form from the site of administration to the blood. Bioavailability is often compared with data from intravenous supply of the drug, in which there are therefore no absorption barriers, and is then referred to as absolute bioavailability.

Absolute bioavailability is defined according to the following formula:

$$F = \frac{AUC_x \cdot D_{iv}}{D_x \cdot AUC_{iv}}$$

where $AUC_x$ is the area-under-the-curve value for the examined formulation, $AUC_{iv}$ is the area-under-the-curve value for an intravenous supply of the drug, $D_x$ is the dose of the drug in the formulation and $D_{iv}$ is the intravenous dose.

The determination of the release profile and the pharmacokinetic parameters is preferably realized through animal trials The most relevant species, owing to its similarity with humans, is the pig. Where the biologically active substance can induce, during the test, an immune response which threatens to affect the determination of the pharmacokinetic parameters for the biologically active substance, inhibition of the immune response should be used, for example by drug treatment. This is known within the technical field, and details can be obtained from the scientific literature, for example Agersó et al, (J,Pharmacol Toxicol 41 (1999) 1–8).

The microparticle preparation according to the invention can be produced by means of a process which comprises:
a) preparation of an aqueous starch solution containing starch, which has an amylopectin content in excess of 85 percent by weight, in which the molecular weight of the said amylopectin is reduced, preferably by shearing, so that at least 80 percent by weight of the material lies within the range 10–10 000 kDa, and which has an amino acid nitrogen content of less than 50 µg per g dry weight of starch, the starch concentration of the solution being at least 20 percent by weight,
b) combining the biologically active substance with the starch solution under conditions such that a composition is formed in the form of a solution, emulsion or suspension of the said substance in the starch solution,
c) mixing the composition obtained in step b) with an aqueous solution of a polymer having the ability to form a two-phase aqueous system, so that an emulsion of starch droplets is formed which contain the biologically active substance as inner phase in an outer phase of the said polymer solution, in which the starch droplets are expediently of the desired size for the microparticles,
d) causing the starch droplets obtained in step c) to gel into starch particles through the natural propensity of the starch to solidify,
e) drying the starch particles, and
f) optionally applying a release-controlling shell of a biocompatible and biodegradable polymer, preferably by an air suspension method, to the dried starch particles.

An important aspect of this process is, in other words, the use of a certain type of starch as microparticle matrix. A starch that is especially suitable, and a process for the production thereof, are precisely described in the Swedish patent application No. 0003616-0. Details of this may in other words be obtained from the said Swedish patent application, the content of which is thus in this respect introduced into the present text by way of reference. Another suitable starch is disclosed in a copending PCT application having the same filing date as the present application and entitled STARCH.

The most important features of such a starch will, however, be described below. In order that fully biodegradable microparticles with high active substance yield shall be formed in a two-phase aqueous system and in order that the obtained starch microparticles shall have the properties to be described below, the starch must generally predominantly consist of highly branched starch, which, in the natural state in the starch granule, is referred to as amylopectin. It should also have a molecular weight distribution which makes it possible to achieve desired concentrations and gelation rates.

It may be added, in this context, that the term "biodegradable" means that the microparticles, after parenteral administration, are dissolved in the body to form endogenic substances, ultimately, for example, glucose. The biodegradability can be determined or examined through incubation with a suitable enzyme, for example alpha-amylase, in vitro. It is in this case appropriate to add the enzyme a number of times during the incubation period, so as thereby to ensure that there is active enzyme permanently present in the incubation mixture. The biodegradability can also be examined through parenteral injection of the microparticles, for example subcutaneously or intramuscularly, and histological examination of the tissue as a function of time.

Biodegradable starch microparticles disappear normally from the tissue within a few weeks and generally within one week. In those cases in which the starch microparticles are coated with a release-controlling shell, for example coated, it is generally this shell which determines the biodegradability rate, which then, in turn, determines when alpha-amylase becomes available to the starch matrix.

The biocompatibility can also be examined through parenteral administration of the microparticles, for example subcutaneously or intramuscularly, and histological evaluation of the tissue, it being important to bear in mind that the biologically active substance, which often is a protein, has in itself the capacity to induce, for example, an immune response if administered in another species. For example, a large number of recombinantly produced human proteins can give rise to an immune response in test animals.

The starch must further have a purity which is acceptable for the manufacture of a parenterally administrable preparation. It must also be able to form sufficiently stable solutions in sufficiently high concentration to enable the biologically active substance to be mixed in under conditions allowing the retention of the bioactivity of the substance, at the same time as it must spontaneously be able to be solidified in a controlled manner in order to achieve stable, yet at the same time biodegradable, microparticles. High concentration of the starch is also important to prevent the biologically active substance from being distributed out to an unacceptable extent to the outer phase or to the interface between the inner and the outer phase.

A number of different embodiments with regard to the character of the starch are as follows.

The starch generally has a purity of less than 50 µg, preferably at most 20 µg, more preferably at most 10 µg, and most preferably at most 5 µg, amino acid nitrogen per g dry weight of starch.

The molecular weight of the abovementioned amylopectin is preferably reduced, such that at least 80% by weight of the material lies within the range of 10–10000 kDa, more preferably 100–4000 kDa, even more preferably 200–1000 kDa, and most preferably 300–600 kDa. Another interesting range in this context may be 10–1000 kDa.

In addition, the starch preferably has an amylopectin content with the reduced molecular weight in question exceeding 95% by weight, better still exceeding 98% by weight. It can also, of course, consist 100% by weight of such amylopectin.

According to another preferred embodiment, the starch is of such a type that it can be dissolved in water in a concentration exceeding 25% by weight. This means, in general, a capacity to dissolve in water according to a technique which is known per se, i.e. usually dissolution at elevated temperature, for example up to approximately 80° C.

According to a further preferred embodiment, the starch is substantially lacking in covalently bonded extra chemical groups of the type which are found in hydroxyethyl starch, By this is meant, in general, that the starch essentially only contains groups of the type which are found in natural starch and have not been in any way modified, such as in hydroxyethyl starch, for example.

Another preferred embodiment involves the starch having an endotoxin content of less than 25 EU/g.

A further preferred embodiment involves the starch containing less than 100 microorganisms per gram, often even less than 10 microorganisms per gram.

For the mixing operation in step b), furthermore, a weight ratio of starch to biologically active substance within the range of 3:1% 10 000:1, preferably 3:1 to 100:1, is expediently used.

It is also the case for the mixing operation that the active substance is mixed with the starch solution before a two-phase aqueous system is formed in step c). The active substance can be in dissolved form, for example in a buffer solution, or in solid, amorphous or crystalline form, and at a suitable temperature, which is generally between room temperature (20° C.) and 45° C., preferably at most 37° C. It is possible to add the starch solution to the biologically active substance, or vice versa. Since the biologically active substances suitable for use in this system, for example proteins, are generally macromolecules, it is possible, when mixing a solution of a dissolved macromolecule with starch, for an emulsion to form, in which the macromolecule generally represents the inner phase, or a precipitate. This is entirely acceptable, provided that the biologically active substance retains or does not appreciably lose its bioactivity. A homogeneous solution, emulsion or suspension is then created by agitation, which can be carried out using a suitable technique. Such a technique is well known in the art, examples which might be quoted being magnetic agitation, propeller agitation or the use of one or more static mixers. An especially preferred embodiment of the invention is represented in this case by the use of propeller agitation.

In the production of the starch microparticles, the concentration of starch in the solution which is to be converted to solid form and in which the biologically active substance is to be incorporated should be at least 20% by weight to enable the formation of starch microparticles having good properties. Exactly that starch concentration which works best in each individual case can be titrated out in a simple manner for each individual biologically active substance, where the load in the microparticles is that which is required in the individual case. In this context, it should be noted that the biologically active substance to be incorporated in the microparticles can affect the two-phase system and the gelation properties of the starch, which also means that customary preparatory trials are conducted for the purpose of determining the optimal conditions in the individual case. Trials generally show that the starch concentration should advantageously be at least 30% by weight and in certain specific cases at least 40% by weight. As the highest limit, 50% by weight is usually applicable, especially at most 45% by weight. It is not normally possible to obtain these high starch concentrations without the use of molecular-weight-reduced, highly branched starch.

Regarding the polymer used in step c) for the purpose of forming a two-phase aqueous system, information is published, within precisely this technical field, on a large number of polymers with the capacity to form two-phase Systems with starch as the inner phase. All such polymers must be considered to lie within the scope of the present invention. An especially suitable polymer in this context, however, is polyethylene glycol. This polyethylene glycol preferably has an average molecular weight of 5–35 kDa, more preferably 15–25 kDa and especially about 20 kDa.

The polymer is dissolved in suitable concentration in water or an aqueous solution, which expression also includes buffer solution, and is temperature-adjusted to a suitable temperature. This temperature lies preferably within the range of 4–50° C., more preferably 10–40° C. and often 10–37° C. The concentration of the polymer in the aqueous solution is expediently at least 20% by weight and preferably at least 30% by weight, and expediently at most 45% by weight. An especially preferred range is 30–40% by weight.

The mixing operation in step c) can be executed in many different ways, for example through the use of propeller agitation or at least-one static mixer. The mixing is normally carried out within the temperature range of 4–50° C., preferably 20–40° C., often about 37° C. In a batch by batch process, the starch solution can be added to the polymer solution or vice versa. Where static mixers or blenders are utilized, the operation is expediently executed by the two solutions being pumped in two separate pipelines into a common pipeline containing the blenders.

The emulsion can be formed using low shearing forces, since there is no high surface tension present between the phases in water/water emulsions, in contrast to oil/water or water/oil emulsions, and in this case it is primarily the viscosity of the starch solution which has to be overcome for the droplets to achieve a certain size distribution. In most cases, magnetic or-propeller agitation is sufficient. On a larger scale, for example when the quantity of microparticles to be produced exceeds 50 g, it is expedient to use so-called baffles to obtain even more effective agitation in the container which is used. An alternative way of forming the water/water emulsion is to use at least one static mixer, the starch solution expediently being pumped at regulated speed in a pipe in which the static mixers have been placed. The pumping can be effected with any type of suitable pump, provided that it gives an even flow rate under these conditions, does not expose the mixture to unnecessarily high shear forces and is acceptable for the manufacture of parenteral preparations in terms of purity and non-leakage of unwanted substances. In those cases, too, in which static mixers are used to create the emulsion, it is generally advantageous to have the solidification into microparticles take place in a vessel with suitable agitation.

A preferred embodiment of the process means that in step e) the polymer solution is added to the composition in at least two stages, in which an admixture is effected after the emulsion has been created or has begun to be created.

It is also within the scope of the present invention, of course, to add the polymer solutions in many stages and to change, for example, the average molecular weight and/or concentration of the polymer used, for example in order to increase the starch concentration in the inner phase where this is desirable.

In the production of the microparticles according to the present invention it is important that the solidification occurs through the natural tendency or capacity of the starch to gel and not, for example, through precipitation with organic solvents, such as acetone. The latter procedure may lead to the biologically active substance being exposed to organic solvent, which in many cases is unacceptable, and to an absence of the natural formation of the physical cross-linkages that are required in order to obtain stable microparticles in a controlled manner.

In connection with the solidification of the microparticles, it is important that this should take place under conditions which are mild for the incorporated biologically active substance(s). In other words, it is primarily a question of using a temperature which is not harmful to the current substance. In this context, it has surprisingly been shown that the criteria for this and for the formation of stable microparticles with suitable size distribution can more easily be met if, during the solidification, more than one temperature or temperature level is used. It is especially advantageous if the solidification process in the two-phase system is initiated at a lower temperature than the temperature which is used in the end phase of the solidification. A preferred embodiment means that the solidification is initiated within the range of 1–20° C., preferably 1–10° C., especially around 4° C., and is concluded within the range of 20–55° C. preferably 25–40° C. especially around 37° C.

Confirmation that the chosen conditions are correct or appropriate can be obtained by establishing that the starch microparticles have a desired size distribution, are stable during the subsequent washing and drying operations and are dissolved substantially by fully enzymatic means in vitro and/or that the incorporated substance has been encapsulated effectively and has retained bioactivity. The last-mentioned is usually examined using chromatographic methods or using other methods established within the art, in vitro or in vivo, after the microparticles have been enzymatically dissolved under mild conditions, and is an important element in ensuring a robust and reliable manufacturing process for sensitive, biologically active substances. It is a great advantage for the microparticles to be able to be fully dissolved under mild conditions, since this minimizes the risks of preparation-induced artifacts, which are usually found when, for example, organic solvents are required to dissolve the microparticles, which is the case, for example, when these consist of a PLGA matrix.

The formed microparticles are preferably washed in a suitable manner in order to remove the outer phase and any surplus active substance. Such washing is expediently effected by filtration, which is made possible by the good mechanical stability and suitable size distribution of the microparticles. Washing by means of centrifugation, removal of the supernatant and resuspension in the washing agent may often also be appropriate, In each washing process, one or more suitable washing agents are used, which generally are buffer-containing aqueous solutions, In this connection, sieving can also be used, if required, in order to adjust the size distribution of the microparticles, for example to eliminate the content of too small microparticles and to ensure that no microparticles above a certain size are present in the finished product.

The microparticles can be dried in any way appropriate, for example by spray-drying, freeze-drying or vacuum-drying. Which drying method is chosen in the individual case often depends on what is most appropriate for the retention of the biological activity for the enclosed biologically active substance. Process considerations also enter into the picture, such as capacity and purity aspects. Freeze-drying is often the preferred drying method, since, correctly designed, it is especially mild with respect to the enclosed biologically active substance. That the incorporated biologically active substance has retained its bioactivity can be established by means of analysis appropriate to the substance after the substance has been enzymatically dissolved under mild conditions. Suitable enzymes for use in connection with starch are alpha-amylase and amyloglucosidase, singly or in combination, it being important to establish, where appropriate, that they are free from possible proteases, which can degrade proteins. The presence of proteases can be detected with methods known within the field and, for example, by mixing the biologically active substance in control trials and determining its integrity in the usual manner after incubation with the intended enzyme mixture under the conditions which will afterwards be used to dissolve the microparticles. Where the preparation is found to contain protease contamination, it can be replaced by a preparation which offers higher purity or is purified from proteases, The enzymes used may need to be purified from contaminating proteases, for example, in order to avoid artifactual degradation of sensitive substances, such as recombinant proteins, for example, incorporated into the microparticles. This can be done using techniques known within the field, for example by chromatography with $\alpha_2$-macroglobulin bonded to suitable chromatographic material.

In order to modify the release properties of the microparticles, a release-controlling shell made from a biocompatible and biodegradable polymer might also be applied. Examples of suitable polymers in this context are found in the prior art, and polymers of lactic acid and glycolic acid (PLGA) can especially be mentioned. The shell in question is preferably applied using air suspension technology. An especially suitable technique of this kind is described in WO97/14408 and details in this regard can thus be obtained from this publication, the content of which is included in the text by reference. The starch microparticles which are obtained by means of the process disclosed above are extremely well suited to coating by means of the said air suspension technology, and the coated microparticles obtained are especially well suited to parenteral administration.

When the produced microparticles are used, either they are coated with a release-controlling outer shell or not, the dry microparticles are suspended in a suitable medium, specifically to permit injection. Such media and processes in these regards are well known within the field and will not need here to be described in further detail. The actual injection can be given through a suitable needle or with a needle-free injector. It is also possible to inject the microparticles using a dry powder injector, without prior resuspension in an injection medium.

Apart from the advantages which have been discussed above, the process described has the advantage that the yield of the biologically active substance is generally high, that it is possible to obtain a very high active substance content in the microparticles whilst retaining the bioactivity of the substance, that the obtained microparticles have the correct size distribution for use for parenteral, controlled (for example delayed or sustained) release, since they are too large to be phagocytized by macrophages and small enough and of such a nature to be injectable, without complications, through small needles, for example 23 G–25 G, as well as injectable using a dry powder injector, and that endogenic and neutral degradation products are formed upon degradation of the microparticles, by which means the active substance, for example, can be prevented from being exposed to an excessively low pH value. Moreover, the process itself is especially well suited to rigorous quality control.

The preparation according to the invention is especially interesting in connection with proteins, peptides, polypeptides, polynucleotides and polysaccharides or, in general, other drugs or biologically active substances which are sensitive to or unstable in, for example, organic solvents, primarily water-soluble substances. Recombinantly produced proteins are a very interesting group of biologically active substances. Hormones, especially human growth hormone, or a growth factor, represent interesting groups of such substances. Generally speaking, however, the invention is not limited to the presence of such substances, since the inventive concept is applicable to any biologically active substance which can be used for parenteral administration. Apart from in connection with sensitivity or instability problems, the invention can thus also be of special interest in such cases where it would otherwise be difficult to remove solvent or where toxicological or other environmental problems might arise.

Classes of biologically active substances to be used are e.g. recombinant proteins, glycosylated recombinant proteins, pegylated recombinant proteins, growth factors, cytokines, blood coagulation factors, monoclonal antibodies, LHRH analogues, and vaccines.

Specific examples of substances are growth hormone, erythropoietin and analogues thereof, interferon ($\alpha$, $\beta$, $\gamma$), blood coagulation factors V-XIII, protein C, insulin and derivatives thereof, macrophage-colony-stimulating factor, granulocyte-colony-stimulating factor, interleukin, glucagon-like peptide 1 or 2, C-peptide, leptin, tumour necrosis factor and epidermal growth factor.

Usable biologically active substances of the non-protein drug type can be chosen from the following groups:

Antitumour agents, antibiotics, anti-inflammatory agents, antihistamines, sedatives, muscle-relaxants, antiepileptic agents, antidepressants, antiallergic agents, bronchodilators, cardiotonic agents, antiarrhythmic agents, vasodilators, antidiabetics, anticoagulants, haemostatic agents, narcotics and steroids.

A preferred non-protein drug is civamide.

The novel microparticle preparation according to the invention is not limited, however, to those which can be produced by means of the said process, but comprises all microparticle preparations of the type in question irrespective of the production methods.

Furthermore, microparticles may consist essentially of starch that has an amylopectin content in excess of 85 percent by weight, of which at least 80 percent by weight has an average molecular weight as defined above, which have an amino acid content of less than 50 µg per g dry weight of starch and which lack covalent chemical cross-linking between the starch molecules.

The starch on which the microparticles in question are based is preferably one of the types of starch defined above in connection with the process.

According to a variant of the microparticles, the bioactivity of the biological substance in these is at least 80%, preferably at least 90% of the bioactivity that the substance exhibited before it was incorporated into the starch. The said bioactivity is most preferably largely retained or preserved in the microparticles.

Yet another variant is represented by microparticles which are biodegradable in vitro in the presence of $\alpha$-amylase and/or amyloglucosidase, Another variant is represented by those that are biodegradable and are eliminated from tissue after subcutaneous or intramuscular administration.

An especially preferred variant of the microparticles is represented by particles which have a release-controlling shell of at least one film-forming, biocompatible and biodegradable polymer.

The said polymer is preferably a homopolymer or copolymer made from $\alpha$-hydroxy acids and/or cyclic diners of $\alpha$-hydroxy acids, the said $\alpha$-hydroxy acid preferably being selected from the group consisting of lactic acid and glycolic acid, and the cyclic dimer preferably being selected from the group consisting of glycolides and lactides.

Such polymers or dimers (of the PLGA type, for example) are precisely described in the prior art, and further details of these may therefore be obtained therefrom.

A further preferred variant of the microparticles is, of course, represented by those microparticles that are obtainable or are produced by means of a process as has been defined above, either in general or in the form of any preferred embodiment of the said process.

As regards the determination of the biological activity for the microparticles containing active substance, this must be carried out in a manner appropriate to each individual biological substance. Where the determination is effected in the form of animal trials, a certain quantity of the biologically active substance incorporated in the starch microparticles is injected, optionally after these microparticles have been previously enzymatically dissolved under mild conditions, and the biological response is compared with the response obtained after injection of a corresponding quantity of the same biologically active substance in a suitable solution. Where the evaluation is made in vitro, for example in test tubes or in cell culture, the biologically active substance is preferably made fully available before the evaluation by the starch microparticles being enzymatically dissolved under mild conditions, after which the activity is determined and compared with the activity for a control solution having the same concentration of the biologically active substance in question. In any event, the evaluation shall include any non-specific effects of the degradation products of the starch microparticles.

The invention will now be explained further with reference to the following non-limiting examples. In these, as in the rest of the text, unless otherwise stated the percentages quoted relate to percentage by weight. Examples 1 to 7 relate to comparative tests, whilst Examples 8 to 15 represent the invention.

EXAMPLES

Examples 1a–1e-b

Control tests: procedure for the production of starch microspheres according to EP 213303 A2. The object of these control tests was to show the state of the art. The starch concentration was generally 5%, and the PEG concentration was 6% (av. mol. wt. 6 kDa). The starch solution (10 g) was poured into the PEG solution (5 g, temperature-adjusted to 70° C.) and stabilized whilst stirring at room temperature overnight. The materials were then resuspended down in 95% ethanol, since it was not possible to filter them. During the various steps, the occurrence of discrete microspheres was observed and, where it was possible, the biodegradability was analyzed in vitro with α-amylase after recovery. Initially attempts were made to recover the microspheres by filtering, but since this was not possible centrifuging (Sorfvall, SS34, 5 min, 10 000 rpm 20° C.) was employed, the supernatant was drawn off and 10 ml of 95% ethanol were added.

Example 1a
Production of Starch Microspheres from Potato Starch.

The potato starch (Acros organics, Lot No. A013642301) formed a clear solution with very high viscosity even at 5%. After stabilizing overnight, discrete microspheres had not been formed, but rather a type of precipitate. After washing with 95% ethanol, no discrete starch microspheres were found, but a rather hard, viscous lump.

Example 1a-b
Production of Starch Microspheres Containing BSA.

Starch microspheres were produced according to example 1a, with the difference that a protein (bovine serum albumin (BSA), 20%, 0.1 ml) was mixed with the starch solution before creation of the two-phase system. After stabilizing overnight, discrete microspheres had not been formed, but rather a type of precipitate, and after washing with 95% ethanol a viscous lump was obtained, but no discrete microspheres.

Example 1b
Production of Starch Microspheres from Soluble Starch.

The soluble starch (Baker BV—Deventer Holland), Lot No. M27602) gave a somewhat opalescent solution when heated to 95° C. No discrete microspheres had been formed after stirring overnight, but a type of precipitate, After washing with 95% ethanol, no discrete microspheres could be observed, but the starch had been precipitated in the form of small gravel-like particles. After drying, approx. 4 mg of particles were obtained out of a total 500 mg of starch prepared. On incubation with (α-amylase in vitro, approx. 65% of the starch matrix was resistant and did not dissolve.

Example 1b-b
Incorporation of BSA into Starch Microspheres Produced from Soluble Starch.

The process according to example 1b was repeated, except that BSA (20%, 0.1 ml) was mixed with the starch solution before creation of the two-phase system. After stabilization overnight, discrete particles had been formed, which were recovered, following which the biodegradability was analyzed in vitro through incubation with α-amylase, with the result that approximately 57% of the matrix was soluble. The protein yield was low and could not be quantified, since the concentration obtained after partial dissolution of the microspheres was lower than the lowest standard in the standard curve for the HPLC method, Example 1c Production of Starch Microspheres from Oxidized, Soluble Starch.

The starch (Perfectamyl A3108, Stadex) formed a clear solution after being heated to 95° C. No discrete microspheres had been formed after stabilization overnight and no solid material at all could be found in the specimen.

Example 1c-b

Incorporation of BSA Into Starch Microspheres Produced from Soluble Starch.

The process according to example 1c was repeated, except that BSA (20%, 0.1 ml) was mixed with the starch solution before creation of the two-phase system. After stabilization, a precipitate was observed, which did not resemble starch, and after washing and drying approx. 2 mg of solid material was obtained.

Example 1d

Production of Starch Microspheres from Native Highly Branched Starch (Amylopectin).

The native amylopectin starch (cerestar SF 04201) gave a clear and viscous solution on heating to 95° C. After stirring overnight, no discrete microspheres could be observed, but the specimen was made up of some sort of precipitate. After washing with 95% ethanol, the specimen had become a slimy mass and contained no discrete starch microspheres.

Example 1d-b

Incorporation of BSA Into Starch Microspheres Produced from Native Highly Branched Starch (Amylopectin).

The process according to example 1d was repeated, except that BSA (20%, 0.1 ml) was mixed with the starch solution before creation of the two-phase system. After stabilization, a precipitate was observed, which did not resemble starch, and after washing and drying a viscous lump was obtained.

Example 1e

Production of Starch Microspheres from Acid-Hydrolyzed and Sheared Amylopectin.

The starch was originally composed of acid-hydrolyzed waxy maize (Cerestar 06090) and was also sheared mechanically in order to give a molecular weight distribution that is better suited to the production of starch microspheres in a two-phase aqueous system. After heating to approx. 95° C. a clear solution was obtained. After stirring overnight, no discrete microspheres could be observed but the specimen consisted of a type of precipitate, After washing with 95% ethanol, no discrete microspheres could be observed but the starch had formed small particles.

Example 1e-b

Incorporation of BSA into Starch Microspheres Produced from Acid-Hydrolyzed and Sheared Starch (Amylopectin).

The process according to example 1e was repeated, except that BSA (20%, 0.1 ml) was mixed with the starch solution before creation of the two-phase system. After stabilization overnight, no discrete microspherer could be observed. On the other hand an extremely small precipitate could be observed. After recovery, the quantity obtained was so small that no precise determination could be undertaken.

Example 2

Production of Starch Microspheres from Amylose.

Starch microspheres were produced from amylose (from Serva) with the aim of analyzing their biodegradability in vitro and in vivo. Since amylose gels too rapidly to permit manual production, a machine was used which permits continuous production. The central unit of the machine is a microwave unit that permits rapid heating of the starch to approx. 150° C., followed by cooling to approx. 45° C. before mixing with protein solution or buffer solution. The starch solution was prepared in distilled water, since otherwise it turns a brown colour when heated in the microwave unit. The starch was composed of pre-gelatinized amylose from peas (4%) and despite repeated homogenizations a number of lumps remained. The flows were adjusted as follows: starch (5 ml/min), Tris buffer, pH 7.8 (1.2 ml/min) and the PEG solution (2.4 percent by weight PEG with an av. mol. wt. of 300, 000 Da) which also contained 6.9% sodium chloride and 14.3% mannitol. The microparticles were allowed to stabilize at room temperature for some hours and then in a refrigerator overnight. They were recovered by successive washings in a centrifuge: three times with 70% ethanol, three times with 5 mm phosphate-buffered common salt solution containing 1 mM calcium chloride and 0.02% sodium azide (pH 7.4), and finally three times with 99.5% ethanol. The microparticles were vacuum-dried, Since there were some very small particles in the preparation, attempts were made to remove these by threefold sedimentations in 99.5% ethanol, which did not result in complete removal of these. A total of 9.5 g of microparticles were obtained and after sedimentation 8.5 g remained.

The particle size distribution was determined with a Malvern Mastersizer and was found to be broad, with the smallest microspheres about 5 μm and the largest over 160 μm. The mean diameter calculated from the volume was 25 μm. Approx. 30–40% of the starch matrix was dissolved when the microspheres were incubated with α-amylase at 37° C. in vitro for two weeks.

This comparative example shows the difficulties involved in producing microspheres from amylose, since it is difficult to make up into homogeneous solutions, requires very high temperatures in order to dissolve and is susceptible to degradation when subjected to these high temperatures, and gels very quickly. The example also shows that the resulting microspheres have far too broad a size distribution both immediately after production and after attempts to narrow the size distribution, and far too high a content of microspheres with a size of less than 10 μm to be well suited to sustained release after subcutaneous or intramuscular injection. The example also shows that the biodegradability, analyzed in vitro, is incomplete over the period of time analyzed.

Example 3
Production of Starch Microspheres Containing β-lactoglobulin.

Starch microspheres were produced from amylose (Serva) in order to analyze the effectiveness of immobilization of a model protein, β-lactoglobulin. Since this amylose gels too rapidly to permit entirely manual production, a machine was used with a microwave unit that permits rapid heating of the starch to approximately 150° C., followed by cooling to around 45° C. before mixing with protein solution or buffer solution. The starch solution (10%) was prepared in distilled water and the flow was set to 5 g/minute. The starch solution (2.5 ml) was collected in a plastic beaker and as the temperature fell to 50–70° C. the protein solution (0.6 ml, 8.3% in buffer) was added thereto under magnetic stirring.

Broadly speaking, immediately thereafter the first PEG solution (10%, av. mol. wt. 20, 000 Da, 3.0 ml) was added to the starch solution under stirring, and after one minute's stirring the second PEG solution (40%, av. mol. wt 20, 000 Da, 10 ml) was added to the emulsion, which was left to stabilize at room temperature until the next day. The microspheres formed were recovered by two different methods in order to demonstrate their capacity to retain an adequate protein loading. The first washing method consisted of centrifuge washings with buffer solutions and resulted in largely all protein leaching out of the starch microspheres. In the second method of recovery, isopropyl alcohol was also used in order to increase the lactoglobulin loading in the microspheres. In this method washing was first performed three times with 70% isopropyl alcohol, then once with 5 mM of phosphate-buffered common salt solution containing 1 mm of calcium chloride and 0.02% sodium azide, then once again with the same buffer before being left to stand in the buffer for one hour with agitation, thereafter 5 times with buffer and finally 3 times with 100% isopropyl alcohol. The microspheres were then vacuum-dried, The protein loading using the isopropyl alcohol wash was 3.6%, which corresponds to a theoretical yield of 18%.

Among other things, the example points to significant practical difficulties in producing microspheres containing protein from amylose, since the starch solution must be subjected to very high temperatures for it to be dissolved completely, since the starch readily undergoes chemical changes at these high temperatures and gels very rapidly after cooling to temperatures that are reasonably low in order to allow the starch solution to be mixed with a sensitive protein. Production is further complicated by the need to use two different solutions of PEG, in order to permit the formation of microspheres and entrapment of the protein therein. A further serious disadvantage is the need to use isopropyl alcohol in the recovery of the microspheres in order to obtain an acceptable protein loading, since most sensitive proteins do not tolerate exposure to this or similar organic solvents. Starch microspheres produced from this amylose are not fully biodegraded by α-amylase either in vitro or in vivo, Example 4
Production of Amylose from Peas Amylose was produced by leaching from starch granules. NUTRIO-P-star 33 (300 g, Nordfalk) was suspended in water (7200 g) and the suspension was heated to 75° C. for one hour. The swollen granules were removed by centrifuging and the solution obtained was filtered, first through a charcoal filter, then a pre-filter (Filtron, 1.5 μm) and finally a sterile filter (Millipore, 0.2 μm). The filtered solution was placed in a refrigerator overnight, the amylose being precipitated and recovered by centrifuging. The precipitate obtained was washed twice with ethanol (95%, 700 ml) and then vacuum-dried. Approximately 30 g of amylose were obtained.

Example 5

Starch microspheres were produced from amylose prepared according to example 4 with a view to analyzing their biodegradability in vitro and in vivo. Since amylose gels too rapidly to permit manual production, a machine was used that permits continuous production. The central unit of the machine is a microwave unit, which permits rapid heating of the starch to approximately 150° C., followed by cooling to around 45° C. before mixing with protein solution or buffer solution. The starch solution was prepared in distilled water, since otherwise it turns a brown colour when heated in the microwave unit. The starch was composed of pregelatinized amylose from peas (4%) and despite repeated homogenizsyions a number of lumps remained. The flows were adjusted as follows: starch (5 ml/min), Tris buffers pH 7.8 (1.2 ml/min) and the PEG solution (2.4 percent by weight PEG with an av. mol. wt. of 300, 000 Da) which also contained 6.9% sodium chloride and 14.3% mannitol. The microparticles were allowed to stabilize at room temperature for some hours and then in a refrigerator overnight. They were recovered by successive washings in a centrifuge: three times with 70% ethanol, three times with 5 mm phosphate-buffered common salt solution containing 1 mm calcium chloride and 0.02% sodium azide, pH 7.4, and finally three times with 99.5% ethanol. The microparticles were vacuum-dried. Since there were some very small particles in the preparation, attempts were made to remove these by threefold sedimentation in 99.5% ethanol, which did not result in complete removal of these. The yield was 8.5 g of particles after the sedimentations, during which 1 g of microspheres was cleaned away.

The particle size distribution was determined with a Malvern Mastersizer and was found to be broad, with the smallest microspheres about 5 µm and the largest over 160 µm. The mean diameter calculated from the volume was 25 µm.

The biodegradability of the starch microspheres was analyzed by incubation with α-amylase in vitro. Initially the degradation was rapid and after one day approximately 35–45% had been converted into soluble form. Thereafter the rate of degradation declined and after 6 days approximately 50% had been dissolved. Thereafter the biodegradability was negligible and after 25 days approximately 50% of the starch microspheres still remained in undissolved form.

This comparative example shows the difficulties involved in producing microspheres from amylose, since it is difficult to make up into homogeneous solutions, requires very high temperatures in order to dissolve and is susceptible to degradation when subjected to these high temperatures, and gels very quickly. The example also shows that the resulting microspheres have far too broad a size distribution, both immediately after manufacture and after attempts to narrow the size distribution, and far too high a content of microspheres with a size of less than 10 µm to be well suited to sustained release after subcutaneous or intramuscular injection. The example also shows that the biodegradability, analyzed in vitro, is incomplete.

Example 6
Analysis of the Biodegradability in vivo of Starch Microspheres Produced from Amylose.
Starch microspheres (3.01 mg) produced from the amylose in example 4 were injected in a volume of 100 µl subcutaneously into the neck of eight rats of the Sprague-Dawley strain that had undergone hypophysectomy. Small nodules could be detected under the skin of all rats at the injection sites 8–9 days after injection. On dissection 9 days after injection, a macroscopic inspection was undertaken in which small white cysts were found at the injection site in all rats. The macroscopic changes were fixed in 4% phosphate-buffered formaldehyde, embedded in paraffin wax, cut up with a nominal thickness of 5 µm. stained with haematoxylin and eosin, and examined under an optical microscope. In the paraffin wax sections in which the starch microspheres could be found, they were seen as eosinophil small spheres surrounded by a zone of granulating tissue containing giant cells and the tissue reaction was characterized as a chronic "granulomatous" inflammation in the subcutaneous tissue. Starch microspheres could also be observed inside macrophages.

The test shows that starch microspheres produced from amylose are found in the subcutaneous tissue 9 days after injection and have thus not been biodegraded sufficiently to have been dissolved during that period, and that in any event a proportion of the microspheres was small enough to allow phagocytosis by macrophages.

Example 7
Analysis of the Biodegradability in Vivo of Starch Microspheres Produced from Amylose.
Starch microspheres produced from amylose according to example 4 and suspended in 10 ml of phosphate-buffered (5 mm) physiological common salt solution (0.15 M), pH 7.2, were injected intramuscularly into the leg of young pigs. Two pigs were dosed with 120 mg of microspheres and two pigs with 600 mg of microspheres. The animals were sacrificed on day 14 and the tissue examined for macroscopic changes and, after the usual embedding and staining processes, for microscopic changes. On day 14 microspheres were found in the tissue to a degree dependent on the dosage. Some microparticles had been subject to phagocytosis by macrophages and giant cells and were to be found intracellularly, which is indicative of very slow degradation of the micropspheres.

The test shows that starch microspheres produced from amylose are found in the intramuscular tissue two weeks after injection, which indicates that the biodegradability of these microspheres is very slow.

Example 7b

Starch microspheres were produced from acid-hydrolyzed amylose from potatoes (Reppal PSM60U), which was subjected to ultrafiltration in order to remove low molecular constituents, with a view to analyzing their biodegradability and capacity to incorporate protein without exposing this to an organic solvent. β-lactoglobulin was used as model protein. The starch concentration was 24% and 4 ml of this were mixed with 1.6 ml of the protein solution, which had a concentration of 50 mg/ml at 37° C., and mixed with PEG (average molecular weight 100 kDa, 15%, 4 ml) and stirred to form an emulsion. The microspheres solidified under stirring at room temperature overnight.

All the protein leached out of the microspheres during the centrifuge washings in the buffer (5 mM sodium phosphate, pH 7.8). If only isopropyl alcohol or a series consisting firstly of 15% PEG with a mol. wt. of 100, 000, followed by 40% PEG with a mol. wt. of 10, 000 Da and finally isopropyl alcohol are used, protein corresponding to between 1.5 and 3% could be found in the microspheres. The biodegradability of the microspheres was analyzed in vitro. This was initially rapid and after twenty-four hours approximately 60% of the matrix had been converted into soluble form. Thereafter the degradation ceased, and after 7 days approximately 70% of the matrix had been biodegraded under these conditions.

In order to obtain some loading of the protein into the said microspheres it was necessary to precipitate the protein with an organic solvent, which is not an acceptable method for sensitive proteins. Nor were the microspheres obtained fully biodegradable in vitro.

Example 7c

Starch microspheres were produced from extensively acid-hydrolyzed amylose from potatoes (Reppal PSM25, Reppe, Glykos, Växjö) with a view to analyzing their biodegradability and capacity to incorporate protein without exposing this to an organic solvent. β-lactoglobulin was used as model protein. The starch concentration war 20% and 4 ml of this were mixed with 1.6 ml of the protein solution, which had a concentration of 50 mg/ml at 37° C. The microspheres solidified under stirring at room temperature overnight.

All the protein leached out of the microspheres during the centrifuge washings in the buffer (5 mM sodium phosphate, pH 7.8). If only isopropyl alcohol or a series consisting firstly of 15% PEG with a mol. wt. of 100, 000, followed by 40% PEG with a mol. wt. of 10, 000 Da and finally isopropyl alcohol are used, protein corresponding approximately to between 1.5 and 2.5% could be found in the microspheres. The biodegradability of the microspheres was analyzed in vitro. This was initially rapid and after twenty-four hours approximately 55% of the matrix had been converted into soluble form. Thereafter the degradation ceased, and after 7 days approximately 70% of the starch matrix had been biodegraded under these conditions.

In order to obtain some loading of the protein into the said microspheres it was necessary to precipitate the protein with an organic solvent, which is not an acceptable method for sensitive proteins. Nor were the microspheres obtained fully biodegradable in vitro.

Example 8
Immobilization of BSA with High Loading in Starch Microspheres Produced from Highly Branched, Sheared Starch.

A starch solution (40%) of sheared, highly branched starch with an av. mol. wt. of 1600 kDa, a solution (38%) of PEG 20 000 Da of av. mol. wt. and a solution of BSA (14%) were prepared in 50 mM sodium phosphate, pH 8.3. The temperature of the starch solution was adjusted to 50–55° C., the PEG and BSA solution to approx. 33° C. The starch solution (2 g) was mixed with the BSA solution (0.7 ml). The solution obtained was drawn up in a spray, which was fitted to a spray pump. A solution of PEG (29 g) was mounted in another spray fitted to another spray pump. The starch microspheres were produced by pumping the mixtures of starch/BSA and PEG through static mixers by means of the spray pump down into a beaker where the emulsion is stirred by a propeller (100 rpm). This part of the process took 2 minutes from starting until everything was mixed. The stirring in the beaker was allowed to continue for 10 minutes and the specimen was then shifted to 4° C., where it was allowed to stand under stirring for approx. 4 hours. Thereafter the pH value of the solution was reduced to approx, 5.5 and the preparation was left at 37° C. overnight without stirring. The starch microspheres were washed by filtering in an Amicon (Amicon ultrafiltration cell) 5 mM sodium phosphate, pH 4.5, and freeze-dried.

The dried microspheres were dissolved by enzyme action with α-amylase and amylo glucosidase for determining the protein and starch yield, and protein loading. The protein yield was 94%, the starch yield 89% and the loading obtained was 10%. The mean particle size determined with a Malvern Mastersizer was 90 µm and with less than 10% of the distribution below 35 µm. By incubation with α-amylase or α-amylase and amylo glucosidase the microspheres were fully dissolved within forty-eight hours.

The example shows that a protein, BSA, van be immobilized with high yield and that the microspheres obtained have a high loading of the protein. The microspheres are biodegradable, since they are completely dissolved by α-amylase in vitro and this can be done under mild conditions, which permits accurate chemical analysis of the immobilized protein without the introduction of artifacts on account of the actual extraction process. The example also shows that all protein entrapped can be recovered after dissolving the microspheres.

Example 9
Immobilization of BSA with High Loading in Starch Microspheres Produced from Highly Branched, Sheared Starch.

Starch microspheres containing BSA were produced by using a starch solution (40%) of sheared highly branched starch with an average molecular weight of 1600 kDa, a PEG solution (38%, av. mol. wt. 20 000 Da) and a solution of BSA (16%) produced in SO mM phosphate, pH 8.3. The temperature of the starch solution was adjusted to 50–55° C. and the PEG and BSA solution to approx. 30° C. The starch microspheres were produced in an IKA reactor (IKA laboratory reactor LR250). The starch solution (20 g) was mixed with the BSA solution (6.7 ml). The PEG solution (290 g) was pumped down into the reactor vessel under stirring (100 rpm) for approx. 6 minutes and the stirring was continued for approx. 15 minutes. The preparation was brought to 4° C. and allowed to stand under stirring overnight. The pH value of the solution was reduced to approx. 5.5 and this was brought to 37° C., where it was allowed to stand for approx. 7 hours without stirring. The starch microspheres containing BSA were washed with 5 mM sodium phosphate, pH 4.5, and freeze-dried.

The dried microspheres were dissolved by enzyme action with α-amylase and amylo glucosidase for determining the protein and starch yield, and protein loading. The protein yield was 99%, the starch yield 91% and the loading obtained was 11.5% The mean particle size determined with a Malvern Mastersizer was 48 µm and with less than 10% of the distribution below 17 µm. By incubation with α-amylase or α-amylase and amylo glucosidase the microspheres were fully dissolved within forty-eight hours.

Example 10
Immobilization of BSA with High Loading in Starch Microspheres Produced from Highly Branched, Sheared Starch.

A starch solution (20%) of highly branched, sheared starch with av. mol. wt. of 1930 kDa, a PEG solution (38%, av. mol. wt. 20 000 Da) and a BSA solution (20%) were prepared in 50 mM sodium carbonate, pH 9.8. The temperature of the starch solution was adjusted to 50–55° C. and the other solutions to approx. 37° C. The starch solution (3 g) was mixed with the BSA solution (0.7 ml). The mixture was drawn up in a syringe and added to the PEG solution (28 g) in a beaker whilst stirring. The preparation was transferred to 4° C., where it was allowed to stand for 4 hours and thereafter to 37° C., where it was allowed to stand overnight. The starch microspheres containing BSA were washed with 5 mM sodium phosphate, pH 4.5, and freeze-dried.

The dried microspheres were dissolved by enzyme action with α-amylase and amylo glucosidase for determining the protein and starch yield, and protein loading. The protein yield was 91%, the starch yield 90% and the loading obtained was 10.6%. The mean particle size determined with a Malvern Mastersizer was 44 µm and with less than 10% of the distribution below 21 µm. By incubation with α-amylase or α-amylase and amylo glucosidase the microspheres were fully dissolved within forty-eight hours.

Example 11
Immobilization of Crystalline hGH in Starch Microspheres Produced from Highly Branched, Sheared Starch with High Starch and PEG Concentrations and Temperature Cycling.

Crystals of zinc hGh were produced according to EP 0 540 582 B1. A suspension of the said crystals was prepared in 10 mM sodium acetate, pH 6.4, containing 2 mM zinc acetate.

A starch solution (40%) was produced from highly branched, sheared starch with av. mol. wt. 378 kDa in 10 mM sodium phosphate, pH 6.4, and a PEG solution with av. Mol. Wt. 20, 000 at a concentration of 30%. This war adjusted to pH 6.4 with 1 M HCl. The temperature of the solutions was adjusted as follows: the starch solution to 50–55° C., the PEG solution to 37° C. and the suspension of Zn-hGH crystals to 37° C. 4.9 g of the starch solution was added to 7 ml of the suspension of Zn-hGH crystals whilst stirring. After approx. 20 seconds, 28 g of the PEG solution was added by means of a spray pump for approx. 6 minutes, whilst continuing to stir at 400 rpm (Eurostar digital). The microspheres began to form immediately and after approx. 15 minutes were moved from 37° C. to 4° C., and were kept there for 4 hours under stirring. After stabilizing for 4 hours, the microspheres were so stable that they could be transferred to 37° C. and kept there without stirring overnight, The microspheres obtained were washed three times with 10 mM sodium acetate, pH 6.4, containing 2 mM zinc acetate, after having been stabilized at 37° C. for approx. 17–20 hours by filtering in an Amicon, and freeze-dried.

The dried microspheres were dissolved by enzyme action with α-amylase and amylo glucosidase for determining the protein and starch yield, protein loading and protein quality. The protein yield was 95.2%, the starch yield 68% and the protein loading in the microspheres was 27.8%. The mean particle size determined with a Malvern Mastersizer was 59 μm and with less than 10% of the distribution below 29 μm. By incubation with (α-amylase or α-amylase and amylo glucosidase the microspheres were fully dissolved within forty-eight hours. The diner content of the protein was 0.75% and polymer content <0.1%.

The test shows that even proteins that have been converted into solid form can be immobilized with high yield and resulting in starch microspheres with high loading of the protein according to the present invention. The test also shows that the starch microspheres obtained can be dissolved under mild conditions, which permits rigorous quality control of the characteristics of the immobilized protein without the introduction of artefacts deriving from trial preparation, and that the protein is not degraded in the process. The protein quality obtained is acceptable for parenteral administration to humans.

Example 12
Immobilization of BSA in Starch Microspheres of Highly Branched, Sheared Starch and Analysis of the Biodegradability in Vivo.

Starch microspheres containing BSA were produced from highly branched, sheared starch with av. mol. wt. 1930 kDa under the following conditions the starch (30%, 100 ml) was mixed with PEG (38%, 1466 ml, av. mol. wt. 20 kDa) and stirred, first for 6 hours at 20° C. and then overnight at 37° C. These were administered subcutaneously and intramuscularly to rats in a dosage of 30 mg in an injection vehicle composed of 0.6% sodium hyaluronic acid (mol. wt, 2000 kDa, Kraeber GmbH, Hamburg) and the injection site was prepared for histological analysis after 3 and 7 days. On day 3, cellular infiltration at the injection site was observed, and these changes had already disappeared by day 7.

This test shows that starch microspheres produced from highly branched, sheared starch are biodegraded rapidly, within one week, in vivo and that the tissue is rapidly normalized.

Example 13
Determination of the Biodegradability of Starch Microspheres in Pigs.

Starch microspheres were produced from sheared starch with an av. mol. wt. of 529 kDa. The starch was weighed into 10 mM of sodium phosphate, pH 6.4, so that the concentration after dissolving was 30% and PEG 20 with an av. mol. wt. in the same buffer so that the final concentration after dissolving was 27%. The solutions were then prepared by autoclaving. Production was performed in an IKA reactor with Eurostar digital stirring control (Labasco). 14.35 g of the starch solution were used for the production and this was kept warm at 50° C. after dissolving, after which 200 g of the PEG solution was fed to the reactor. The emulsion was formed by stirring at 160 rpm with a propeller and after 8 minutes the stirring speed was adjusted to 140 rpm, and after 5 hours to 110 rpm, and the temperature was set to 20° C. for 7 hours and thereafter 38° C. for 17 hours. The starch microspheres obtained were then washed (Amicon ultrafiltration unit 8400) four times with 300 ml of water and freeze-dried. The dry starch microspheres were sieved (Retsch sieving machine) with 38 and 100 μm screens. The total quantity of starch microspheres that was obtained prior to sieving was 3.61 g, which corresponds to a yield of approximately 86%, and after sieving 2.54 g, which corresponds to a yield of approx. 59%.

The starch microspheres were resuspended in 1 ml of 0.11% sodium hyaluronic acid, 4% mannitol, in water for injection and 100 mg of microspheres were injected subcutaneously into pigs. The injection site was prepared for histological evaluation. No starch microspheres could be observed 7 days after injection.

This test shows that the starch microspheres were biodegraded rapidly and disappeared from the injection site within one week.

Example 14
Production of Coated Starch Microspheres Containing hGH in Starch Microspheres Produced from Highly Branched, Sheared Starch with Temperature Cycling, Coating Thereof and Analysis of their Capacity for Controlled Release of the Entrapped Protein after Parenteral Administration to Pigs.

Starch microspheres containing crystalline hGH were produced according to example 11.

The starch microspheres obtained were coated with a release-controlling shell of PLGA by means of an air suspension method according to WO97/14408 using different shell compositions in order to obtain different release rates. The following mixtures of PLGA were used; Batch 1 (-■-) 75% RG502H and 25% RG756, Batch 2 (-□-) 60% RG502H and 40% RG756, Batch 3 (-○-) 75% RG504H and 25% RG756, and Batch 4 (-Δ-) 100% RG504H.

The pharmacokinetics of hGH were analyzed in pigs, the immune system reactivity of which was suppressed by oral administration of cyclosporin A (20 mg/kg), azathioprine (2 mg/kg) and prednisolone (2 mg/kg) in order to avoid the formation of antibodies to the human growth hormone that might affect the pharmacokinetics. The coated microspheres were administered subcutaneously in the neck with a 19 G needle in a dosage of 1.25 mg hGH/kg. Five pigs were studied for each formulation. Blood samples were taken prior to injection and after 0.02, 0.04, 0.08, 0.17, 0.25, 0.33 days and daily thereafter until the study was completed 29 days after dosing. The hGH serum concentration was determined. FIG. 1 below shows the mean value for the hGH serum concentration that was obtained for the different formulations.

The test shows that starch microspheres coated with PLGA after parenteral administration to pigs give rise to a controlled, prolonged release of hGH. The hGH concentrations obtained are generally in excess of the level 0.2 ng/ml which induces increased levels of the insulin-like growth factor (IGF-1), which is an indicator of biological effect, in humans, (Putney, Current Opinion in Chemical Biology 1998, 2:548–552). The example also shows that the pharmacokinetics of hGH may be varied significantly by varying the composition of the coating shell, The example furthermore shows that, compared to parenteral prolonged release preparations previously available, exceptionally low initial release, so-called burst, can be achieved. The test also shows that high levels of bioavailability can generally be achieved, in the range of 19–52%, and with an exceptionally high proportion, 72–96%, in the prolonged release phase, which occurs after the initial release, the so-called "burst".

The analysis of hGH in plasma was carried out according to Agersö et al. (J. Pharmacol Toxicol 41 (1999) 1–8).

Example 15

The following example shows how a formulation can be optimized for controlled release by mixing two different formulations with different characteristics.

Starch microspheres containing human growth hormone were produced firstly according to example 14, except that the loading obtained for Batch 1 and Batch 2 was 7.7 and 7.6% respectively and Batch 1 was coated with a single polymer, RG502H (Boehringer Ingelheim), and solid particles of zinc carbonate were mixed in the coating emulsion used to create the inner third of the coating, whilst Batch 2 was coated with a polymer mixture composed of 75% RG502H and 25% RG756 (Boehringer Ingelheim).

The release of the protein incorporated into the microspheres was studied in rats that had been subjected to hypophysectomy (MOL:Wist). The microspheres were suspended in a solution containing 0.15% hyaluronic acid, 30 mM sodium phosphate buffer pH 7.4 containing 80 mM NaCl. The animals were injected with a volume of 200 μl subcutaneously in the neck using an 18G needle. Five animals per batch were injected. The dosage was 750 μg hGH/animal. Blood samples (250 μl) were taken from the orbital plexus under carbon dioxide anaesthesia. Serum was extracted and stored at −18° C. The serum samples were analyzed for growth hormone by means of a specific growth hormone antibody-based IRMA method (Tandhem-R hGH, Hybritech).

Figure 2A:
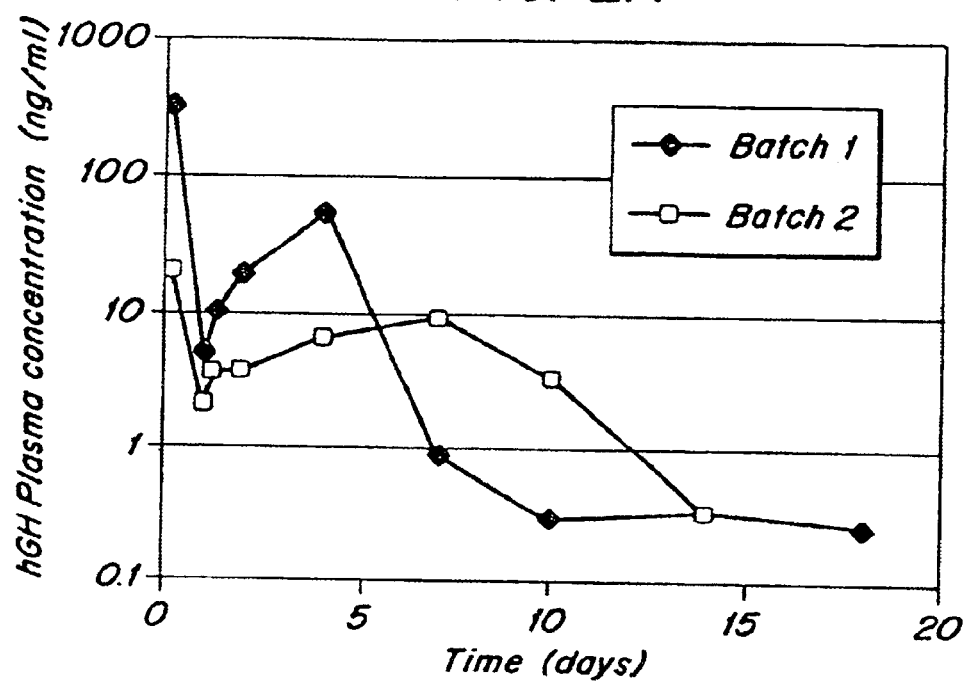
Figure 2B:
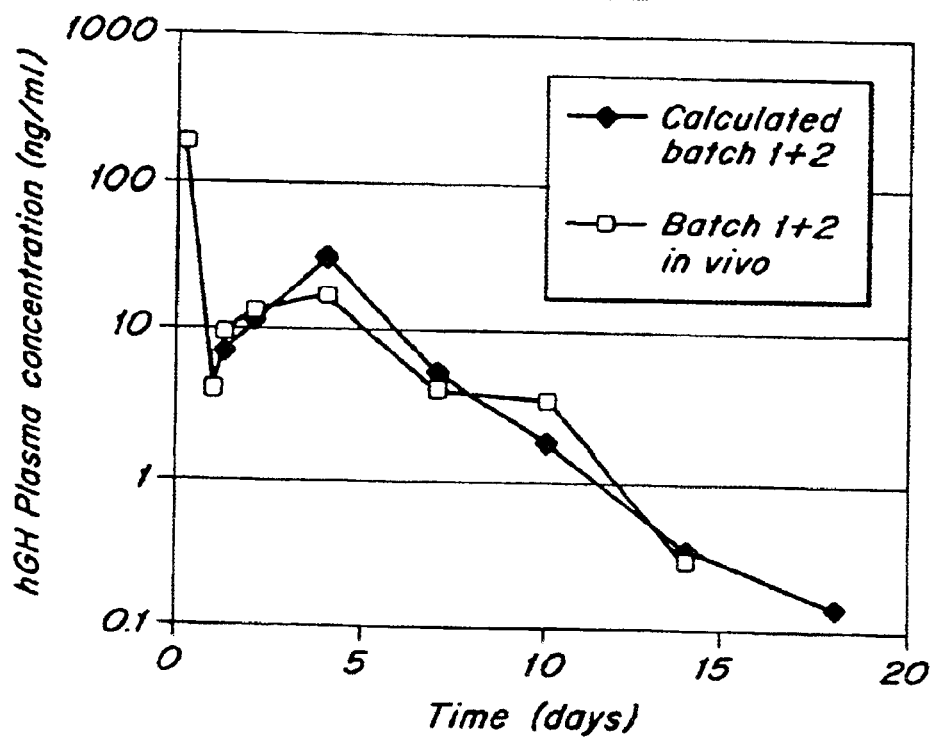

After Batch 1 and 2 had been tested and analyzed in the animal model and a plasma concentration curve had been compiled, it was calculated how a plasma concentration curve would appear if Batch 1 and 2 were mixed in equal parts. The value was calculated individually by taking the mean value of the plasma concentration for the two batches at each point in time. The test described above was then repeated with a mixture of the two. The plasma concentration curve obtained was compiled and this has been plotted in FIGS. 2A and 2B. This shows that by controlled mixing of two batches with different release characteristics it is possible to obtain a desired release profile and concentration of the biological active substance in serum or plasma.

What is claimed is:

1. A parenterally administrable, biodegradable microparticle preparation containing a biologically active substance that is sensitive to or unstable in organic solvents, in which the microparticles are substantially composed of sheared, highly branched starch, which has an amylopectin content in excess of 85% by weight, of which at least 80% by weight has an average molecular weight in the range of 10–10 000 kDa, and which exhibits a release of the biologically active substance in which the bioavailability of said substance is at least 35% of the bioavailability that is obtained when the substance in question is injected intravenously in soluble form.

2. A preparation according to claim 1, in which the starch has an amino acid nitrogen content of less than 50 μg per g dry weight of starch and which lacks covalent chemical cross-linking between the starch molecules.

3. A preparation according to claim 1, in which said bioavailability is at least 45%, preferably at least 50% of the bioavailability that is obtained when the biologically active substance is injected intravenously.

4. A parenterally administrable, biodegradable microparticle preparation containing a biologically active substance that is sensitive to or unstable in organic solvents, in which the microparticles are substantially composed of sheared, highly branched starch, which has an amylopectin content in excess of 85% by weight, of which at least 80% by weight has an average molecular weight in the range of 10–10 000 kDa, and which exhibits a release of the active substance characterized in that in the release that takes place during any continuous seven-day period the quotient between the highest serum or plasma concentration of the biologically active substance divided by the mean concentration during said seven-day period is less than 5, provided that the chosen seven-day period does not include the first 24 hours after injection.

5. A preparation according to claim 4, in which the starch has an amino acid nitrogen content of less than 50 μg per g dry weight of starch and which lacks covalent chemical cross-linking between the starch molecule.

6. A preparation according to claim 4, in which said release is less than 4 times, preferably less than 3 times, and more preferably less than twice.

7. A parenterally administrable, biodegradable microparticle preparation containing a biologically active substance that is sensitive to or unstable in organic solvents, in which the microparticles are substantially composed of sheared, highly branched starch, which has an amylopectin content in excess of 85% by weight, of which at least 80% by weight has an average molecular weight in the range of 10–10 000 kDa, and which exhibits a release of the biologically active substance in which the mean residence time for said biologically active substance is at least 14 days.

8. A preparation according to claim 7, in which the starch has an amino acid nitrogen content of less than 50 μg per g dry weight of starch and which lacks covalent chemical cross-linking between the starch molecules.

9. A preparation according to claim 7, in which said mean residence time is at least 7 days, preferably at least 9 days, more preferably at least 11 days, and most preferably at least 13 days.

10. A preparation according to claim 1, in which the microparticles are substantially composed of starch, which has an amylopectin content in excess of 85% by weight, of which at least 80% by weight has an average molecular weight in the range of 10–100000 kDa, which has an amino acid nitrogen content of les than 50 μg per dry weight of starch and which lack covalent chemical cross-linking between the starch molecules.

11. A preparation according to claim 1, in which said average molecular weight is in the range of 100–4000 kDa, preferably 100–1000 kDa.

12. A preparation according to claim 1, in which said average molecular weight is in he range of 200–1000 kDa, preferably 300–600 kDa.

* * * * *